US010357510B2

(12) United States Patent
Goodson, III et al.

(10) Patent No.: US 10,357,510 B2
(45) Date of Patent: Jul. 23, 2019

(54) METAL NANOCLUSTERS AND USES THEREOF

(71) Applicant: THE REGENTS OF THE UNIVERSITY OF MICHIGAN, Ann Arbor, MI (US)

(72) Inventors: Theodore Goodson, III, Ann Arbor, MI (US); Oleg Varnavski, Ypsilanti, MI (US); Sung Hei Yau, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/501,243

(22) PCT Filed: Aug. 7, 2015

(86) PCT No.: PCT/US2015/044116
§ 371 (c)(1),
(2) Date: Feb. 2, 2017

(87) PCT Pub. No.: WO2016/022870
PCT Pub. Date: Feb. 11, 2016

(65) Prior Publication Data
US 2017/0216348 A1    Aug. 3, 2017

Related U.S. Application Data

(60) Provisional application No. 62/034,285, filed on Aug. 7, 2014.

(51) Int. Cl.
| | |
|---|---|
| *B82Y 5/00* | (2011.01) |
| *C09D 5/32* | (2006.01) |
| *C09D 7/61* | (2018.01) |
| *A61K 33/00* | (2006.01) |
| *A61K 41/00* | (2006.01) |
| *C08K 3/014* | (2018.01) |
| *G01N 33/58* | (2006.01) |

(52) U.S. Cl.
CPC .......... *A61K 33/00* (2013.01); *A61K 41/0057* (2013.01); *C08K 3/014* (2018.01); *C09D 5/32* (2013.01); *C09D 7/61* (2018.01); *G01N 33/587* (2013.01); *B82Y 5/00* (2013.01); *Y10S 977/773* (2013.01)

(58) Field of Classification Search
CPC ...... B82B 3/009; C22F 1/14; Y10T 428/2982; A61K 33/00; B82Y 5/00; C09D 7/61; Y10S 977/773
See application file for complete search history.

(56) References Cited

U.S. PATENT DOCUMENTS

| | | | |
|---|---|---|---|
| 5,731,365 A | 3/1998 | Engelhardt et al. | |
| 2007/0178511 A1* | 8/2007 | Leung ................ | A61K 41/0057 435/6.12 |
| 2008/0118912 A1 | 5/2008 | Dickson et al. | |
| 2013/0183665 A1* | 7/2013 | Chan ..................... | A61K 33/24 435/6.1 |

FOREIGN PATENT DOCUMENTS

| | | |
|---|---|---|
| EP | 703 265 A1 | 3/1996 |
| WO | WO-2006/082242 A2 | 8/2006 |
| WO | WO-2006/097389 A2 | 9/2006 |
| WO | WO-2010/009106 A1 | 1/2010 |
| WO | WO-2013/173458 A1 | 11/2013 |

OTHER PUBLICATIONS

Thomas et al (Accounts of Chemical Research, 2003, vol. 36, pp. 888-898).*
Qian et al (Chemistry of Materials, 2011, vol. 23, pp. 2209-2217).*
Devadas et al., Unique Ultrafast Visible Luminescence in Monolayer-Protected Au25 Clusters, J. Phys. Chem. C, 114(51):22417-23 (2010).
Goodson et al., Optical properties and applications of dendrimer-metal nanocomposites, Int. Rev. Phys. Chem., 23:109-50 (2004).
International Preliminary Report on Patentability, International Application No. PCT/US2015/044116, dated Feb. 7, 2017.
International Search Report and Written Opinion, International Application No. PCT/US2015/044116, dated Dec. 3, 2015.
Lin et al., Synthesis, characterization, and bioconjugation of fluorescent gold nanoclusters toward biological labeling applications, ACS Nano, 3(2):395-401 (2009).
Mathew et al., Noble metal clusters: applications in energy, environment, and biology, Particle & Particle Systems Characterization, pp. 1-37 (2014).
Mroz et al., Cell death pathways in photodynamic therapy of cancer, Cancers (Basel):3(2):2516-39 (2011).
Ramakrishna et al., Quantum-sized gold clusters as efficient two-photon absorbers, J. Am. Chem. Soc., 130(15):5032-3 (2008).
Varnavski et al., Critical size for the observation of quantum confinement in optically excited gold clusters, J. Am. Chem. Soc., 132(1):16-7 (2010).
Varnavski et al., Optically excited acoustic vibrations in quantum-sized monolayer-protected gold clusters, ACS Nano, 4(6):3406-12 (2010).
Varnavski et al., Ultrafast time-resolved photoluminescence from novel metal-dendrimer nanocomposites, J. Chem. Physics, 114:1962 (2001).
Wenseleers et al., Five orders of magnitude enhancement of two-photon absorption for dyes on silver nanoparticle fractal clusters, J. Phys. Chem. B, 106:6853-63 (2002).
Yau et al., An ultrafast look at Au nanoclusters, Acc. Chem. Res., 46(7):1506-16 (2013).

(Continued)

*Primary Examiner* — Mark V Stevens
(74) *Attorney, Agent, or Firm* — Marshall, Gerstein & Borun LLP

(57) ABSTRACT

Provided herein are metal nanoclusters, having a high absorption to volume ratio, and uses of the same, such as in generating singlet oxygen, or in protecting surfaces from high intensity light.

10 Claims, 5 Drawing Sheets

(56) References Cited

OTHER PUBLICATIONS

Yau et al., Bright two-photon emission and ultra-fast relaxation dynamics in a DNA-templated nanocluster investigated by ultra-fast spectroscopy, Nanoscale, 4(14):4247-54 (2012).
Yau et al., Ultrafast Optical Study of Small Gold Monolayer Protected Clusters: A Closer Look at Emission, J. Phys. Chem. C, 114(38):15979-85 (2010).

* cited by examiner

Metal Nanoclusters Conjugate
Periodic Table of the Elements

| | | | | | | | | | | | | | | | | | |
|---|---|---|---|---|---|---|---|---|---|---|---|---|---|---|---|---|---|
| hydrogen 1 H 1.0079 | | | | | | | | | | | | | | | | | helium 2 He 4.3026 |
| lithium 3 Li 6.941 | beryllium 4 Be 9.8122 | | | | | | | | | | | boron 5 B 10.811 | carbon 6 C 12.011 | nitrogen 7 N 14.007 | oxygen 8 O 15.999 | fluorine 9 F 8.998 | neon 10 Ne 20.180 |
| sodium 11 Na 22.990 | magnesium 12 Mg 24.305 | | | | | | | | | | | aluminium 13 Al 26.982 | silicon 14 Si 28.086 | phosphorus 15 P 30.974 | sulfur 16 S 32.065 | chlorine 17 Cl 35.452 | argon 18 Ar 39.948 |
| potassium 19 K 39.098 | calcium 20 Ca 40.078 | scandium 21 Sc 44.956 | titanium 22 Ti 47.867 | vanadium 23 V 50.942 | chromium 24 Cr 51.996 | manganese 25 Mn 54.938 | iron 26 Fe 55.845 | cobalt 27 Co 58.933 | nickel 28 Ni 58.693 | copper 29 Cu 63.546 | zinc 30 Zn 65.38 | gallium 31 Ga 69.723 | germanium 32 Ge 72.64 | arsenic 33 As 74.922 | selenium 34 Se 78.96 | bromine 35 Br 79.904 | krypton 36 Kr 83.798 |
| rubidium 37 Rb 85.468 | strontium 38 Sr 87.62 | yttrium 39 Y 88.906 | zirconium 40 Zr 91.224 | niobium 41 Nb 92.906 | molybdenum 42 Mo 95.96 | technetium 43 Tc [98] | ruthenium 44 Ru 101.07 | rhodium 45 Rh 102.91 | palladium 46 Pd 106.42 | silver 47 Ag 107.87 | cadmium 48 Cd 112.41 | indium 49 In 114.82 | tin 50 Sn 118.71 | antimony 51 Sb 121.76 | tellurium 52 Te 127.60 | iodine 53 I 126.90 | xenon 54 Xe 131.29 |
| caesium 55 Cs 132.91 | barium 56 Ba 137.33 | 57-70 * | lutetium 71 Lu 174.57 | hafnium 72 Hf 178.49 | tantalum 73 Ta 180.95 | tungsten 74 W 183.84 | rhenium 75 Re 186.21 | osmium 76 Os 190.23 | iridium 77 Ir 192.22 | platinum 78 Pt 195.08 | gold 79 Au 196.97 | mercury 80 Hg 200.59 | thallium 81 Tl 204.38 | lead 82 Pb 207.2 | bismuth 83 Bi 208.98 | polonium 84 Po [209] | astatine 85 At [210] | radon 86 Rn [222] |
| francium 87 Fr [223] | radium 88 Ra [226] | 89-102  | lawrencium 103 Lr [262] | rutherfordium 104 Rf [261] | dubnium 105 Db [262] | seaborgium 106 Sg [246] | bohrium 107 Bh [264] | hassium 108 Hs [277] | meitnerium 109 Mt [268] | ununnilium 110 Uun [271] | unununium 111 Uuu [273] | ununbium 112 Uub [277] | | ununquadium 114 Uuq** [289] | | | | |

| | lanthanum 57 La 138.91 | cerium 58 Ce 140.12 | praseodymium 59 Pr 140.91 | neodymium 60 Nd 144.24 | promethium 61 Pm [145] | samarium 62 Sm 150.36 | europium 63 Eu 151.96 | gadolinium 64 Gd 157.25 | terbium 65 Tb 158.93 | dysprosium 66 Dy 162.50 | holmium 67 Ho 164.93 | erbium 68 Er 167.26 | thulium 69 Tm 168.93 | ytterbium 70 Yb 173.05 |
|---|---|---|---|---|---|---|---|---|---|---|---|---|---|---|
| *lanthanoids | | | | | | | | | | | | | | |
| actinoids | actinium 89 Ac [227] | thorium 90 Th 232.04 | protactinium 91 Pa 231.04 | uranium 92 U 238.03 | neptunium 93 Np [237] | plutonium 94 Pu [244] | americium 95 Am [243] | curium 96 Cm [247] | berkelium 97 Bk [247] | californium 98 Cf [251] | einsteinium 99 Es [252] | fermium 100 Fm [257] | mendelevium 101 Md [258] | nobelium 102 No** [259] |

Metal Atoms – Functional Group – Linker – Ligand

FIG. 1

Metal Nanosystems
Metal Nanosystems

2nm < n <~200nm

2nm > n

Metal Nanoparticles (NP)
- Well known colloidal gold
- Quasiband structure
- Possesses strong surface plasmon resonance in the visible region

Metal Nanoclusters (NC)
- Discrete energy level
- Long-lived excited state
- No plasmonic resonance

HA/V MNC

High Absorption to Volume NC
- Absorption to volume ratio of $10^7 m^{-1}$ or higher
- Under linear or non-linear excitation
- Can be used in photodynamic therapy

FIG. 2

METAL NANOCLUSTERS AND USES THEREOF

SUMMARY

Provided herein are conjugates comprising a metal nanocluster having at least a portion of the surface of the metal nanocluster modified with a moiety having a structure -X-Lk-Lg; wherein the metal nanocluster comprises less than 200 metal atoms and has a size of less than 2 nm; Lk is $C_{1-50}$alkylene, wherein the carbon backbone optionally has one or more heteroatoms selected from O, NH, and S; X is a functional group capable of attaching to the metal nanocluster surface; and Lg is a ligand selected from the group consisting of a peptide, a protein, an oligonucleotide, a fluorophore, and a chromophore. In some cases, X comprises an alcohol, an ether, a thiol, a phosphate, a phosphonate, phosphinate, or a carboxylate.

The metal nanoclusters as used herein can exhibit an absorption to volume ratio of at least $10^7$ m$^{-1}$ under linear or non-linear excitation, have an excited state longer than 10 psec, and exhibit no plasmonic resonance. In various cases, the metal nanoclusters exhibit an absorption to volume ratio of at least $10^7$ m$^{-1}$ under each of linear and non-linear excitation. In various cases, the metal nanoclusters have a size about 1 nm to less than 2 nm. The metal of the nanoclusters can comprise silver, gold, cobalt, nickel, platinum, copper, iron, molybdenum, or bismuth. In some cases, the metal is a Group IX metal, Group X metal, Group XI metal, Group XII metal, or Group XIII metal. In various cases, the metal nanoclusters are $Au_{144}$, $Au_{25}$, $Ag_{15}$, $Ag_{32}$, $Ag_{44}$, or a combination thereof. In some cases, the metal nanoclusters are $Au_{25}$ or $Au_{144}$, while in other cases, the metal nanoclusters are $Ag_{15}$, $Ag_{32}$, or $Ag_{44}$.

In some cases, the ligands comprise oligonucleic acids, proteins, or a combination thereof. In various cases, the oligonucleic acids are DNA or RNA. The proteins can comprise serum albumin. In some cases, the ligand is a chromophore, and in some specific cases, the chromophore is a two-photon chromophore. In some cases, the ligand is a fluorophore.

Also provided herein are compositions comprising the conjugates disclosed herein. The compositions disclosed herein can further comprise one or more of nanoparticles and photosensitive agents (e.g., chromophore or fluorophore). In various cases, the composition of conjugates is a liquid composition. The liquid composition can comprise a polar solvent. In some cases, the liquid composition comprises a nonpolar solvent. In some cases, the composition of conjugates is a solid composition. In various cases, the solid composition is in the form of a film or coating. The film or coating can further comprise a coating agent. The film can comprise a polymer selected from the group consisting of polyvinylpyrrolidone, polyvinyl alcohol, poly-methyl methacrylate, polystyrene, polyethylene oxide, polyethylene glycol, and a mixture thereof. In various cases, the coating or film has a thickness of about 2 nm to about 1 µm.

Further provided are methods of protecting a material from light comprising applying a composition as disclosed herein to at least a portion of the materials surface or admixing the composition with the material. In some cases, the material is a lens, metal, glass, or detector. The composition can be a paint. The composition can provide a first absorption ratio for a first wavelength range of 300 nm to 800 nm and a second absorption ratio for a second wavelength range of 800 nm to 2000 nm.

Further provided is a method of generating singlet oxygen comprising exposing a composition as disclosed herein to light having a wavelength of about 300 nm to about 2000 nm. The light can have a wavelength of about 800 nm to about 1600 nm. In some cases, the light is for two photon excitation. In various cases, the metal nanoclusters generate singlet oxygen through non-linear excitation. In some cases, the metal nanoclusters generate singlet oxygen through linear excitation. In some cases, the nanocluster has a singlet oxygen generation rate of at least 0.05 $^1O_2$/nanocluster/min at a concentration of about 10 nM to about 500 µM. In various cases, the singlet oxygen generation rate is at least 2 $^1O_2$/nanocluster/min at a concentration of about 10 nM to about 1 µM. In various cases, the method can further comprise contacting a cell with the composition as disclosed herein thereby killing the cell. The cell can be, e.g., a cancer or bacterial cell. The contacting can be in vitro. In some cases, the contacting can be in vivo. The contacting can comprise administering the composition to a subject suffering from cancer or suffering from a bacterial infection. In various cases, the subject is further exposed to the light to generate singlet oxygen. In various cases, the methods disclosed herein are performed in the absence of a photosensitive agent, such that the singlet oxygen is generated by the metal nanoclusters. In some cases, the photosensitive agent is $C_{60}$, a metal nanoparticle; a porphyrin, or a chlorophyll. More specific examples of contemplated photosensitive agents include photofrinI, photofrinII, methyl blue, new methyl blue, and rose Bengal.

BRIEF DESCRIPTION OF FIGURES

FIG. 1 shows a metal nanocluster as disclosed herein, with a metal core and a ligand coating. The metal core can be any one of the metals highlighted in the corresponding periodic table, and the ligand can be one or more of the classes noted (thiol, carboxylic acid, phosphate, alcohol, nucleic acid, and protein).

FIG. 2 shows the difference between nanoparticles (NPs) and nanoclusters (NCs). Metal nanoclusters have discrete energy levels, long-lived excited state and the lack of plasmonic resonance. High Absorption to Volume NC has an absorption to volume ratio that is unusually higher under linear or non-linear excitation.

DETAILED DESCRIPTION

Metal nanoclusters (MNC) are metal systems smaller than 2 nm, which can form various shape, sizes. The MNCs disclosed herein can have a size of less than about 2 nm. In various cases, the MNC has a size of about 1 nm to less than 2 nm.

Figure 3:
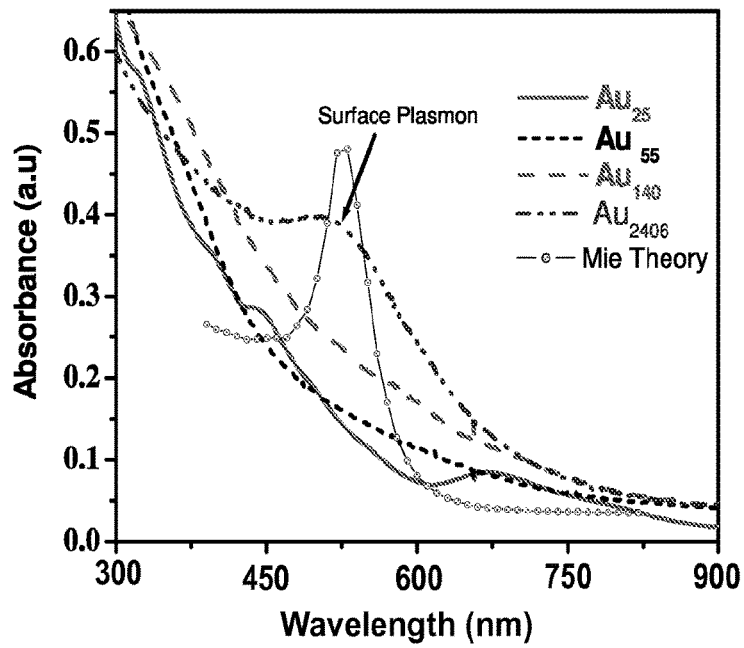
FIG. 3 shows an absorption spectrum for various nanoclusters, compared to a nanoparticle (Mie Theory). Comparison of a nanoparticle ($Au_{2406}$) and the metal nanoclusters highlight the lack of surface plasmon for nanoclusters.
Figure 4:
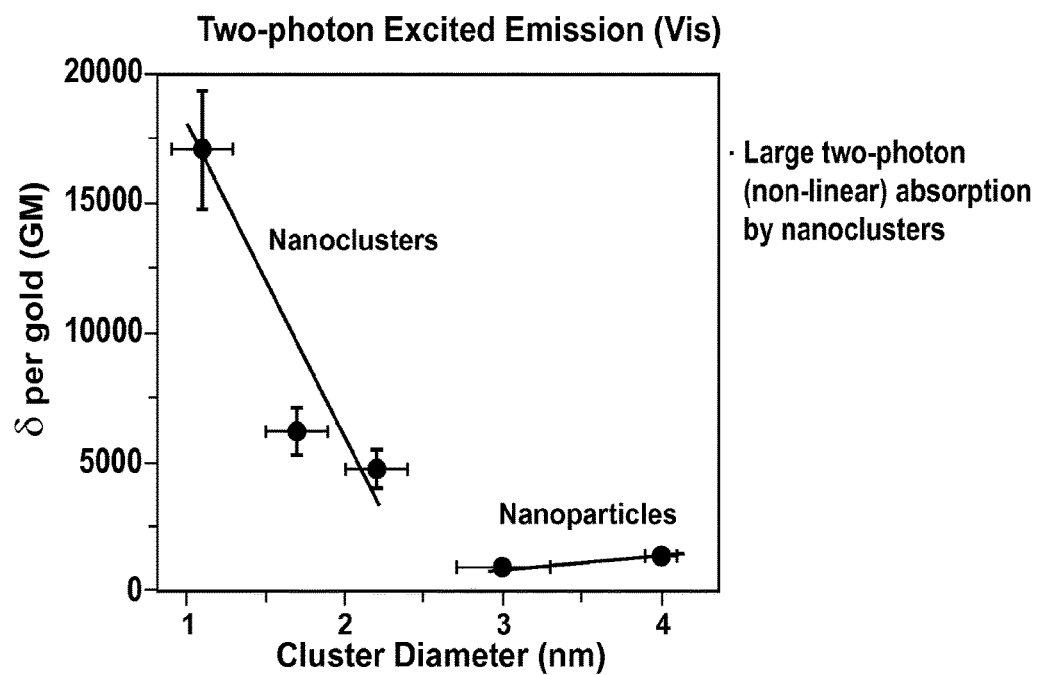
FIG. 4 shows the two-photon absorption of nanoclusters, based upon cluster diameter, compared to nanoparticles. The high absorption to volume ratio is unique to nanocluster under linear or non-linear absorption. The high non-linear absorption cross-section of metal nanoclusters, compared to that of nanoparticles, is shown. The high absorption allows for the different optical applications possible for this material.

MNCs can include Monolayered Protected Metal Clusters (MPCs). MPCs are a class of small (e.g., less than about 2 nm) stable metal constructs that are water and organic solvent soluble.[1-9] MNCs are different from metal nanoparticles because of their physical, electronic and optical properties.[1] MNCs exhibit no plasmonic effects (e.g., no plasmonic resonance as seen in FIG. 3), which is in contrast to metal nanoparticles, and MNCs have molecular like behavior such as emission.[1] Within different types of MNCs, there are certain sizes, configurations and compositions that can result in an unusually high (or higher) absorption to volume ratios (HA/V), such as, for example, $1 \times 10^7$ $m^{-1}$ or greater. High absorption to volume ratio is not common among metal nanoclusters; most metal nanoclusters have much lower absorption to volume ratio, usually on the order of $10^6$ or lower. In various cases, the MNCs and MPCs disclosed herein have a A/V ratio of at least $1 \times 10^7$ $m^{-1}$. In various cases, the A/V is at least $2 \times 10^7$ $m^{-1}$, at least $3 \times 10^7$ $m^{-1}$, at least $4 \times 10^7$ $m^{-1}$, at least $5 \times 10^7$ $m^{-1}$, at least $7 \times 10^7$ $m^{-1}$, or at least $8 \times 10^7$ $m^{-1}$. In various cases, the A/V is about $1 \times 10^7$ to about $1 \times 10^8$ $m^{-1}$. The high A/V ratio (HA/V) can be exhibited under either linear or non-linear excitation. In some cases, the high A/V ratio is exhibited under both linear and non-linear excitation.

One such HA/V-MNC is $Au_{144}(-X-Lk-Lg)_{60}$, composed of 144 gold atoms, covered by 60 ligands (attached to the surface of the MNC through the -X-Lk group), $Au_{144}$ is about 1.7 nm in size. Other MNCs contemplated comprise a metal selected from silver, gold, cobalt, nickel, platinum, copper, iron, molybdenum, and bismuth, or a metal in Group IX, Group X, Group XI, Group XII, or Group XIII of the periodic table (e.g., see FIG. 1). In some cases, the metal is aluminum, tin, magnesium, copper, silver, nickel, iron, cobalt, magnesium, platinum, palladium, iridium, vanadium, silver, rhodium, ruthenium, or a combination thereof. The metal core of the MNC (e.g., as seen in FIG. 1) is comprised of a select number of metal atoms that can arrange into a stable orientation, almost similar to that of a molecule, such that the metal cluster is a closed structure. Some specific MNC arrangements include $Au_{25}$, $Au_{144}$, $Ag_{15}$, $Ag_{32}$, and $Ag_{44}$.

The ligand (both homogeneous and heterogeneous) of the MNC may include thiols (e.g., $C_{1-50}$alkyl-SH), carboxylic acids (e.g., R—$CO_2$H, where R is a $C_{1-50}$ alkyl, $C_{2-50}$alkenyl, $C_{2-50}$alkynyl, aryl, heteroaryl, aryl-$C_{1-50}$alkyl, or heteroaryl-$C_{1-50}$alkyl), phosphate, nucleic acid (e.g., DNA or RNA having about 10 to 100 nucleobases), and proteins (e.g., having 5 to 1000, or 5 to 500 amino acids, or specifically, e.g., serum albumin). The type and number of ligands can be easily determined by the person of skill in the art. Some specifically contemplated ligands include serum albumin, DNA, RNA, $C_5$-$C_{30}$ alkane thiols, silica oxide, silica, and $C_6$-$C_{30}$ alcohols.

The ligand (e.g., the peptide, protein, oligonucleotide, fluorophore, or chromophore) can be attached to at least a portion of the MNC surface through a functional group X and a linker (Lk) comprising a $C_{1-50}$alkylene moiety. The functional group X is one suitable for attachment to, e.g., forming a covalent bond or non-covalent interaction with, the surface of the MNC. Suitable functional groups include an alcohol, an ether, a thiol, a phosphate, a phosphonate, phosphinate, or a carboxylate. The linker can be a $C_{1-50}$alkylene, wherein the carbon backbone optionally has one or more heteroatoms selected from O, NH, and S.

Examples of chromophores as ligands of the conjugates disclosed herein include alizarin, punicin, pyrroles, porphyrins, lycopene, β-carotene, anthocyanins, chlorophyll, tetrapyrrole, bilirubin, urobilin. The chromophore can be a two-photon chromophore, such as Rhodamine, Coumarin, crystal voliet, porphone, chlorophyll.

Examples of fluorophores as ligands of the conjugates disclosed herein include xanthene, fluorescein, rhodamine, coumarin, anthracene, aanthraquinones, oxazine, nile red, nile blue, cresyl violet, arylmethine, crystal violet, malachite green, porphin, phthalocyanine, bilirubin.

Compositions

In some cases, the conjugates of MNCs disclosed herein can be in a liquid composition. For example, the MNCs can be in an aqueous solution, a polar organic solvent (e.g., ethanol, methanol, isopropanol, ethyl acetate, DMSO, DMF), or a nonpolar solvent (e.g., THF, methylene chloride, hexanes, toluene).

In some cases, the MNCs disclosed herein can be in a solid form, e.g., a film or coating. The film or coating can have a thickness of about 2 nm to about 1 μm. In some cases, the thickness is about 5 nm to about 500 nm, or about 10 nm to about 100 nm. In some cases, the thickness can be greater than 1 μm, e.g., up to 10 μm or greater. The film can comprise a polymer selected from polyvinylpyrrolidone, polyvinyl alcohol, poly-methyl methacrylate, polystyrene, polyethylene oxide, polyethylene glycol, or a mixture thereof.

The solid composition can further comprise a coating agent, nanoparticles, and/or a photosensitive additive (e.g., a chromophore or a fluorophore).

Contemplated coating agents include metal phosphates, inorganic particles, and water soluble polyvalent metal salts. Water soluble polyvalent metal salts include aluminum sulfate, aluminum nitrate, aluminum chloride, potassium aluminum sulfate, sodium aluminum sulfate, magnesium sulfate, magnesium citrate, magnesium lactate, zirconium sulfate, zirconium lactate, iron lactate, iron citrate, calcium acetate, calcium propionate, calcium citrate, calcium lactate, strontium lactate, zinc lactate, zinc sulfate, zinc citrate, aluminum lactate, aluminum acetate, aluminum formate, calcium formate, strontium formate, and strontium acetate.

The coating agent may further comprise water-insoluble metal phosphates or other inorganic particles, for example silica, clay, or mica, which can be applied as powders or as aqueous dispersions. Suitable water-insoluble metal phosphates are for example phosphates which can be deemed to be "phosphates" in the technical sense, such as phosphate oxides, phosphate hydroxides, phosphate silicates, phosphate fluorides or the like. As used herein, the term "water-insoluble" denotes a solubility of less than 10 g, e.g. of less than 1 g or less than 0.1 g in 1000 ml of water at 25° C. Suitable water-insoluble metal phosphates include pyrophosphates, hydrogen phosphates and phosphates of calcium, of magnesium, of strontium, of barium, of zinc, of iron, of aluminum, of titanium, of zirconium, of hafnium, of tin, of cerium, of scandium, of yttrium or of lanthanum, and also mixtures thereof. For example, contemplated water-insoluble metal phosphates include calcium hydrogenphosphate, calcium phosphate, apatite, Thomas flour, berlinite ($AlPO_4$) and Rhenania phosphate.

Solid compositions of MNCs disclosed herein can further comprise a film-forming agent. Suitable film-forming agent agents include those disclosed in U.S. Pat. No. 5,731,365 and in EP 0703265, and also in WO 2006/082242 and WO 2006/097389. The film-forming agent can be, e.g., polyurethanes, poly(meth)acrylates, which optionally can be cross-linked by e.g. Zn, polyacrylates, and copolymers of styrene-(meth)acrylate, and copolymers of styrene and/or (meth) acrylate comprising acrylonitrile, copolymers of butadiene-styrene and/or acrylonitrile, (co)polymers of (cross-linkable) N-Vinylpyrrolidone and (co)polymers of vinylacetate and mixtures thereof. The film-forming agent may be applied as aqueous dispersion, and optionally coalescing agents and/or anti-oxidants may be added.

Photosensitive additives, as used herein, refer to materials that are unstable or reactive when exposed to light. In some cases, the additive is sensitive when exposed to a specific wavelength or range of wavelengths, and in various cases, when exposed to any light. Instability of the additive can be by decomposition or degradation of the material. Reaction of the additive can be generation of an acid, base, free radical, or the like. Some examples of photosensitive additives include dyes, diazonaphthoquinone compounds, photo-acid generators, photo-base generators, free radical generators, or combinations thereof.

The disclosed MNCs, and compositions thereof, have many applications, it can be used for high efficiency photodynamic therapy though the generation of singlet oxygen under liner and/or non-linear excitation at visible and near infrared wavelengths.

MNCs can also be used in places where large absorption of photons is required in a small volume such as coatings under normal or high intensity of solar or artificial lighting conditions.

Synthesis

The synthesis of the metal nanocluster conjugates can be organized into three different synthesis regimes: (1) synthesis of the metal nanocluster conjugates without modification to the conjugate. The conjugate with the structure functional group, linker and ligand is synthesized before reaction with the metal ions to from the metal nanocluster conjugate; (2) modification of the ligand on the metal nanocluster conjugate; and (3) replacement of the conjugate.

An exemplary synthesis is performed as noted specifically here, but can be applied to different ligands, linkers, and functional groups. The example conjugate of N-(2-mercaptoethyl)pyrene-1-carboxamide follows known procedure as follows: A solution of 1-pyrenecarboxylic acid (0.7 g, 2.8 mmol) in dichlormethane (30 ml) and oxalyl chloride (0.42 g, 3.4 mmol) is prepared and 0.15 ml of DMF is added, the reaction mixture was stirred for 2 hours at room temperature. After the reaction, the solvent was evaporated. The product was added to 20 ml of THF, which was added to a solution of cysteamine hydrochloride (0.29 g, 1.27 mmol) and sodium hydroxide (0.23 g, 5.7 mmol). The reaction mixture was stirred for 12 hours. The product is washed with water and THF, then filtered and added to a solution of sodium borohydride (0.96 g, 25.4 mmol), and stirred at 90 C for 2 hours. The final mixture is cooled to room temperature and pH adjusted to 2 with HCL. Solvent is removed, and the product is extracted with chloroform and dried. The final product is dissolved in hexane.

$Au_{25}$ with 18 conjugates is synthesized starting with 0.5 g of $HAuCl_4$ dissolved in 10 mL solvent of $H_2O$, 0.9 g of TOABr in 40 mL toluene is added to the reaction. The solution was placed in an ice bath. The conjugated (N-(2-mercaptoethyl)pyrene-1-carbozamide) was added to the solution in excess and stirred. A freshly prepared $NaBH_4$ solution (0.485 g, 10 mL $H_2O$) was quickly added. The solution turned black and the reaction was allowed to stir for 30 min. The aqueous phase was removed and the toluene solution was washed with copious amount of water. The metal nanocluster conjugates were extracted with acetone. The acetone was evaporated and the metal nanocluster conjugates were washed with ethanol and acetonitrile.

After the synthesis of the metal nanocluster conjugate, the ligand on the conjugate can be made with a terminal group that allows for further modification. For example a carboxylic acid ligand group can be substituted to an amide group via a amide-forming coupling reaction. The metal nanocluster conjugate is dissolved in THF and treated with 20 equivalent of BOP, HOBt, NMM, and DMAP for the carbon activation. After the activation, a 10 equivalents of amine is added and stirred for 15 hours. The resulted solution is dried to remove the solvent and additional solvent washes were used to achieve high purity.

Complete conjugate on a metal nanocluster conjugate can be exchanged. The metal nanocluster conjugate and the new conjugate is solvated in the same solvent. The exchange can occur through thermos dynamic means in room temperature. For example $Au_{25}$ with a simple conjugate compost of a thiol, a 4 carbon chain and a benzene can be changed to a conjugate of N-(2-mercaptoethyl)pyrene-1-carboxamide. The $Au_{25}$ conjugate and the new conjugate is mixed in a 1:5 molar ration in toluene. The reaction mixture is stirred for 2 hours. The resultant solution was then ultra-centrifuged and washed with toluene repeatedly to free from the excess ligand.

Material characterization: Steady-state Absorption Spectrum is a major tool in the identification of metal nanocluster conjugates (MNC) from metal nanoparticles. Due to the quantum confinement nature of the small metal system, MNC exhibit no plasmonic resonance (FIG. 3), which is commonly found in larger metal nanoparticles such as $Au_{2406}$ (FIG. 3). Plasmonic resonance can be modeled by the Mie theory, in the case of MNCs, the model predicts the resonance frequency to be near 500 nm. The SPR at 500 nm is not observed for MNCs. $Au_{25}$, $Au_{55}$ and $Au_{140}$ have no plasmonic resonance. Additionally, MNCs has discrete absorption spectrum, which is absorption peaks or shoulders in the absorption spectrum, in the case of MNC $Au_{25}$, absorption peak at 400 nm, 450 nm and 680 nm are discreet transitions unique to this MNC. While the spectrum for nanoparticle $Au_{2406}$ lack these features and is instead broad.

Figure 5:
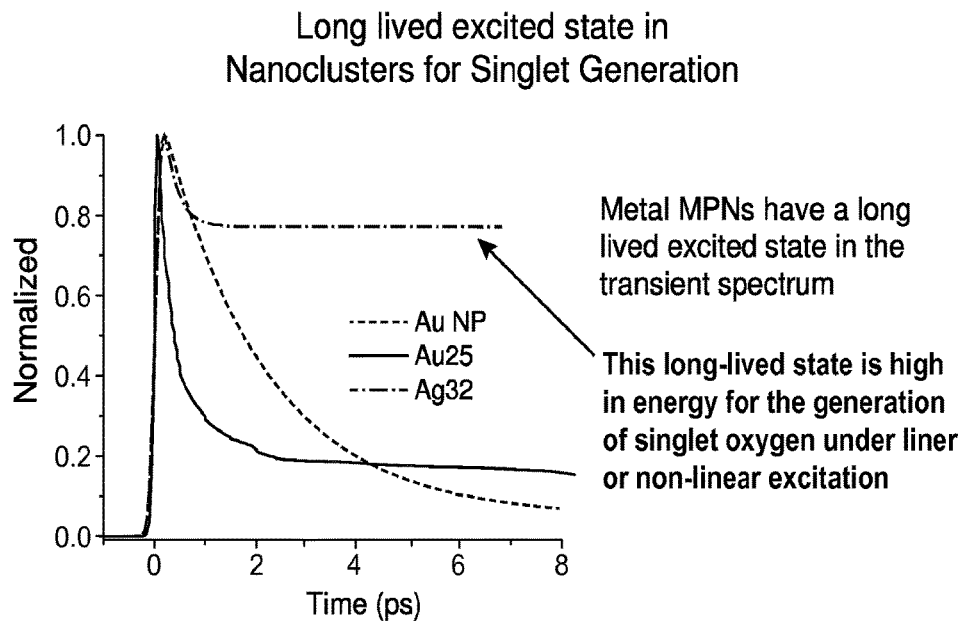
FIG. 5 shows the long lived excited state in nanoclusters beneficial for singlet oxygen generation. Transient absorption spectrum measures the excited state dynamics of this system. The excited state dynamics of metal nanoclusters shows a long-lived state that could lead to the singlet oxygen generation under linear or non-liner excitation.
Figure 6:
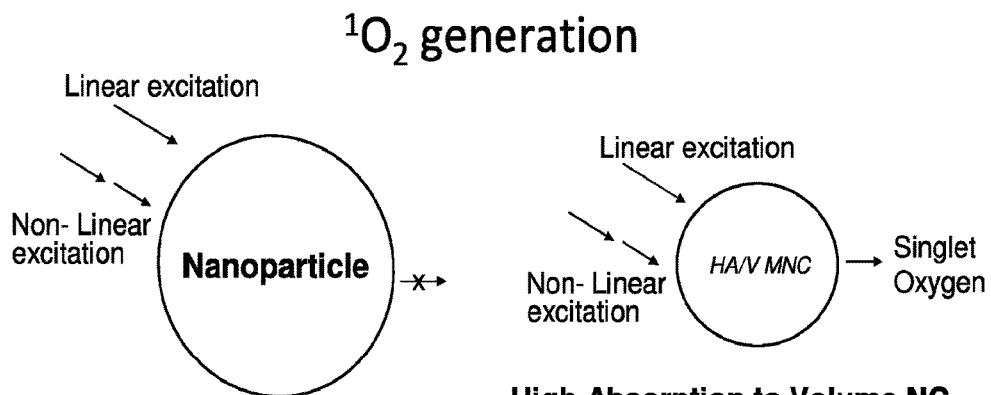
FIG. 6 shows that singlet oxygen can be generated by high absorption to volume nanoclusters under linear or non-linear excitation. Metal nanoparticles are not able to generate single oxygen under the same condition.
Figure 7:
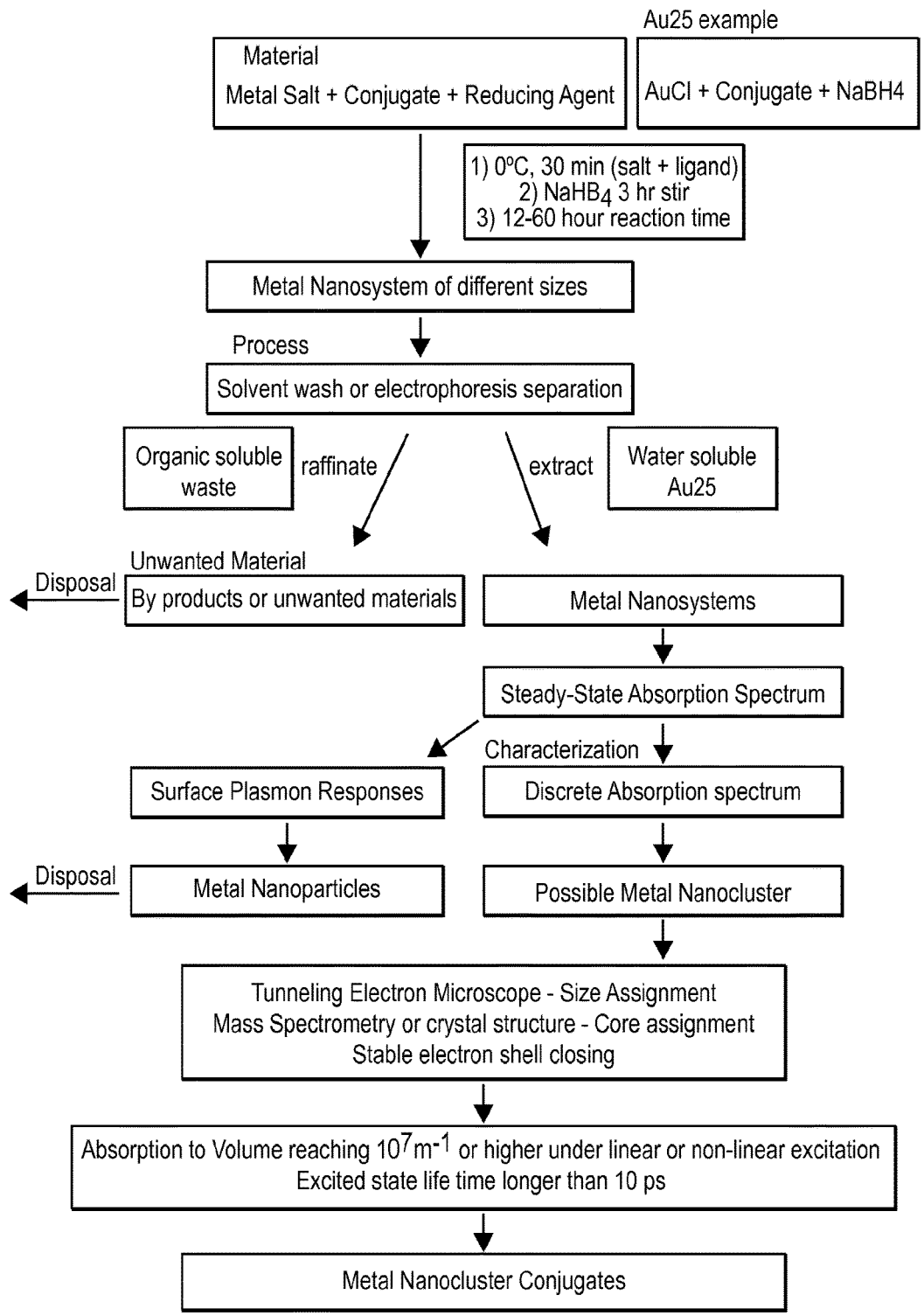
FIG. 7 shows a scheme for nanoclusters formation, characterization, and various applications.

The singlet oxygen generation ability of MNC is the result of the measurable long-lived excited state. This long-lived excited state is not found in larger nanoparticles as seen in FIG. 5. The long lived excited state can be identified using ultrafast transient absorption spectroscopy. After excitation by a pulse laser at 400 nm, the change in absorption is measured using transient absorption spectroscopy. The trace of the excited state with respect to time shows the excitate state live time. Shown in FIG. 5, the example nanoparticle have an excited state that decays within 5 pico second, while MNC $Au_{25}$ and $Ag_{32}$ have very long lived excited state, longer than 10 ps. The disclosed MNCs have a long lived excited state which leads to the generation of singlet oxygen.

Biological Applications

The MNCs in solution can enter cells due to their small size, as they can pass the cell membrane. The cell is exposed to visible and near infrared excitation. Under excitation in the visible or infrared (e.g., 300 nm to 2000 nm light, or 800 nm to 1600 nm light, or 400 nm to 1600 nm light), MNCs can generate singlet oxygen. In some cases, the light is two-photon light. In various cases, the MNCs generate singlet oxygen through multi-photon non-linear excitation. In some cases, the MNCs generate singlet oxygen through linear excitation.

The possibility of singlet oxygen generation originates from the possible long-lived state observed only for metal nanoclusters by transient absorption spectroscopy. The long-lived state is not observed for metal nanoparticles. Direct generation of singlet oxygen would classify this treatment as a type II photodynamic therapy. Singlet oxygen is a highly reactive oxygen species which can undergo other reactions in cells. Singlet oxygen in cells can lead to cell death.[10]

MNCs present a new type of material very different from traditional systems such as organic photosensitizers or photosensitized nanoparticles. MNCs can generate singlet under excitation without additional modification. MNCs have high stability and low toxicity. Due to the small size of MNCs (e.g., less than about 2 nm), they can deeply penetrate the cell. The high absorption cross-section of HA/V-MNCs can also lead to more effective treatment. In some cases, the MNCs have a singlet oxygen rate of at least 0.05 $^1O_2$/nanocluster/min at a concentration of about 10 nM to about 500 μM, or at least 2 $^1O_2$/nanocluster/min at a concentration of about 10 nM to about 1 μM.

The development of MNCs with a high absorption to volume ratio for biological application has not been explored. Typical MNCs has an absorption cross section to volume ratio of $3 \times 10^6$ m$^{-1}$. HA/V-MNCs would be a new class of materials designed for direct photodynamic therapy with a much higher absorption cross-section to volume ratio of $7 \times 10^7$ m$^{-1}$. HA/V-MNCs can be functionalized through conjugation with specific bio-markers for specific cellular targeting. It could also be used without conjugation for use in a large area.

MNCs with a high A/v ratio are capable of generating singlet oxygen to a greater extent than nanoparticles, or MNCs not having a high A/V ratio. An initial study of $Au_{25}$, $Ag_{32}$ MNCs and nanoparticles, compared to MNCs having a A/V of at least $10^7$ m$^{-1}$ using singlet oxygen traps 1,3-Diphenylisobenzofuran (DPBF) showed that HA/V-MNCs have a performance gain of 100 times in singlet oxygen generation rate per cluster per minute over regular MPCs under the same condition. The initial study used a 532 nm excitation by a laser at 50 mW average power, and the solutions were exposed to the excitation light for up to 30 minutes (accumulated). The change in the absorption of the DPBF at 400 nm was used to calculate the rate of singlet oxygen. Results are shown in Table 1.

TABLE 1

| Material | Absorption to Volume Ratio | Concentration | $^1O_2$/cluster/min |
|---|---|---|---|
| $Au_{25}$ | $3.38 \times 10^6$ m$^{-1}$ | $2 \times 10^{-5}$ M | 0.03 |
| HA/V-MNC ($Au_{144}$) | $7.42 \times 10^7$ m$^{-1}$ | $5 \times 10^{-7}$ M | 3.20 |
| $Ag_{32}$ | $6.97 \times 10^6$ m$^{-1}$ | $3 \times 10^{-5}$ M | 0.02 |

TABLE 1-continued

| Material | Absorption to Volume Ratio | Concentration | $^1O_2$/cluster/min |
|---|---|---|---|
| Au NP (40 nm) | $1 \times 10^8$ m$^{-1}$ | Literature | Thermal heating + fragmentation (0.378, estimated) |

Figure 8:
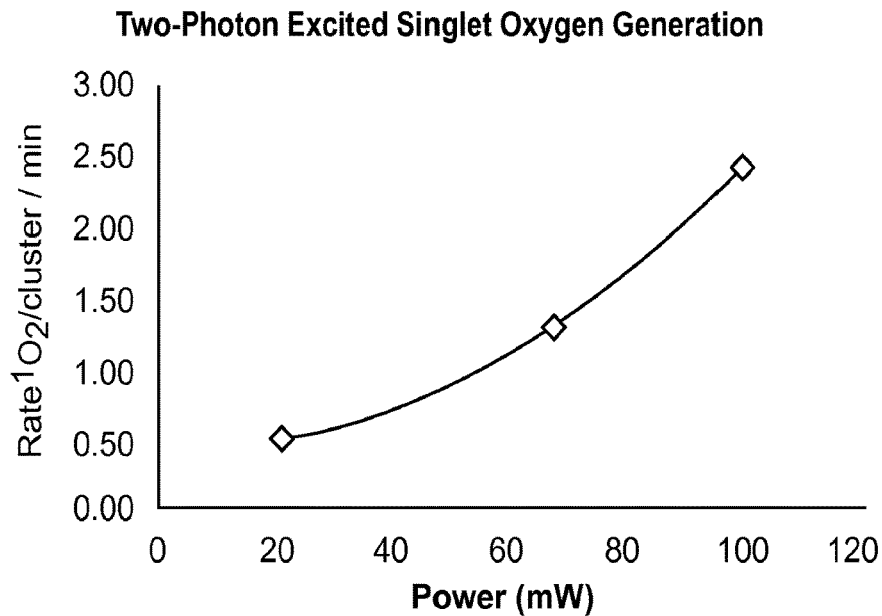
FIG. 8 shows two-photon excited singlet oxygenation rate compared to input power, showing a nonlinear increase in singlet oxygen generation as a function of power.

In addition to one-photon (linear) excitation of the conjugates disclosed herein, two-photon (non-linear) excitation can be used to generate singlet oxygen. The use of two-photon excitation allows for infrared excitation, which can be 800 nm or longer and allows for much deeper tissue penetration in biological systems. Two-photon absorption cross-section of MNCs are order of magnitude higher than organic photosensitizers. Two photon excitation is achieved with a high intensity pulsed laser excited at 800 nm. $Au_{25}$ is tested at various powers. Without the MNC, there is no detectable singlet oxygen generation under 800 nm excitation. Singlet oxygen generation under two photon excitation has a rate that is 2 orders of magnitude higher than one photon excitation under similar average power, about 70 mw for the case of $Au_{25}$. This high rate of singlet oxygen generation can be used for high efficiency, high penetration photodynamic therapy. Since $Au_{144}$ and other MNC has similar absorption cross-section, similar high singlet oxygen generation rate is expected. Results are shown in Table 2, and in FIG. 8.

TABLE 2

| Power | Concentration | $^1O_2$/cluster/min |
|---|---|---|
| 21 mW | $2 \times 10^{-5}$ M | 0.5 |
| 68 mW | $5 \times 10^{-7}$ M | 1.3 |
| 100 mW | $3 \times 10^{-5}$ M | 2.4 |

Both one-photon (linear) and two-photon (non-linear) excitation of the HA/V-MNCs and MPCs was tested. The use of two-photon excitation allows for infrared excitation such as 800 nm or longer of the MNCs. An advantage of two-photon non-linear excitation in the infrared is that incident radiation that would otherwise experience high absorption in tissue of a biological system (e.g., a human), can be made to penetrate much deeper into the tissue by the two-photon conversion process. The two-photon absorption cross-section of MNCs has been reported to be an order of magnitude higher than organic photosensitizers. Initial studies indicate that two-photon excitation of MPCs (including HA/V-MNCs) can produce singlet oxygen at rates comparable to one-photon excitation. Additionally, the rate of singlet oxygen generation increases non-linearly as a function of power, which allows for high light intensity high performance photodynamic therapy using non-linear effects.

A low concentration of metal nanocluster conjugates was used to control the absorption spectra so that the absorption of the metal nanoclusters would not interfere with the characteristic absorption of the DPBF. A selected excitation of 523 nm was chosen so that only the MNC is excited. The laser was operated at 100 mW which is further reduced to 50 mW through the use of a natural density filter. The samples are placement into the holder, after which the shutter is open and timed for excitation. The absorption spectrum of the sample is taken after the exposure. The entire experiment has to be performed in the dark to eliminate unwanted excitation. The study found that MNC generate about 0.02-0.03 singlet oxygen per cluster per minute (table 1). Literature on Au nanoparticle (AU NP) about 40 nm shows that no singlet oxygen is generated and reported cell death is due to thermal heating or the fragmentation of the nanoparticles under excitation. The singlet oxygen property is unique to MNCs. Due to this ability of MNCs, no further modification of the MNC is need for singlet oxygen generation. For nanoparticles it is necessary to attach materials that allow for singlet oxygen generation. The presently disclosed conjugates of MNC are stable and no degradation due to laser excitation was observed. In the various MNCs, $Au_{144}$ shows the largest singlet oxygen generation rate, which is a result of the high absorption to volume ratio. The high singlet oxygen generation rate can be used for low light photodynamic generation of singlet oxygen, which can result in lower dosage or lower exposure time for the same therapeutic impact. The singlet oxygen generation for MNCs can be used in photodynamic therapy, where specific photoexcitation of a targeted area can be used to treat various forms of cancer. MNCs can also be used for antibacterial treatment. MNCs have high stability and low toxicity, which are important attributes for a photo-activated drug.

The MNCs can be administered to a patient who would benefit from exposure to singlet oxygen. In some cases, the patient suffers from cancer or a bacterial infection and the singlet oxygen kills the cancer cell or bacteria. In some cases, the MNCs are administered then the patient is exposed to linear and/or non-linear light to generate singlet oxygen. In some cases, the light absorption is non-linear.

In some aspects, the cancer comprises a solid tumor, for example, a carcinoma and a sarcoma. Carcinomas include malignant neoplasms derived from epithelial cells which infiltrate, for example, invade, surrounding tissues and give rise to metastases. Adenocarcinomas are carcinomas derived from glandular tissue, or from tissues that form recognizable glandular structures. Another broad category of cancers includes sarcomas and fibrosarcomas, which are tumors whose cells are embedded in a fibrillar or homogeneous substance, such as embryonic connective tissue. The invention also provides methods of treatment of cancers of myeloid or lymphoid systems, including leukemias, lymphomas, and other cancers that typically are not present as a tumor mass, but are distributed in the vascular or lymphoreticular systems. Further contemplated are methods for treatment of adult and pediatric oncology, growth of solid tumors/malignancies, myxoid and round cell carcinoma, locally advanced tumors, cancer metastases, including lymphatic metastases. The cancers listed herein are not intended to be limiting. Age (child and adult), sex (male and female), primary and secondary, pre- and post-metastatic, acute and chronic, benign and malignant, anatomical location cancer embodiments and variations are contemplated targets. Cancers are grouped by embryonic origin (e.g., carcinoma, lymphomas, and sarcomas), by organ or physiological system, and by miscellaneous grouping. Particular cancers may overlap in their classification, and their listing in one group does not exclude them from another.

Carcinomas that may targeted include adrenocortical, acinar, acinic cell, acinous, adenocystic, adenoid cystic, adenoid squamous cell, cancer adenomatosum, adenosquamous, adnexel, cancer of adrenal cortex, adrenocortical, aldosterone-producing, aldosterone-secreting, alveolar, alveolar cell, ameloblastic, ampullary, anaplastic cancer of thyroid gland, apocrine, basal cell, basal cell, alveolar, comedo basal cell, cystic basal cell, morphea-like basal cell, multicentric basal cell, nodulo-ulcerative basal cell, pigmented basal cell, sclerosing basal cell, superficial basal cell, basaloid, basosquamous cell, bile duct, extrahepatic bile duct, intrahepatic bile duct, bronchioalveolar, bronchiolar, bronchioloalveolar, bronchoalveolar, bronchoalveolar cell, bronchogenic, cerebriform, cholangiocelluarl, chorionic, choroids plexus, clear cell, cloacogenic anal, colloid, comedo, corpus, cancer of corpus uteri, cortisol-producing, cribriform, cylindrical, cylindrical cell, duct, ductal, ductal cancer of the prostate, ductal cancer in situ (DCIS), eccrine, embryonal, cancer en cuirasse, endometrial, cancer of endometrium, endometroid, epidermoid, cancer ex mixed tumor, cancer ex pleomorphic adenoma, exophytic, fibrolamellar, cancer fibro'sum, follicular cancer of thyroid gland, gastric, gelatinform, gelatinous, giant cell, giant cell cancer of thyroid gland, cancer gigantocellulare, glandular, granulose cell, hepatocellular, Hiirthle cell, hypernephroid, infantile embryonal, islet cell carcinoma, inflammatory cancer of the breast, cancer in situ, intraductal, intraepidermal, intraepithelial, juvenile embryonal, Kulchitsky-cell, large cell, leptomeningeal, lobular, infiltrating lobular, invasive lobular, lobular cancer in situ (LCIS), lymphoepithelial, cancer medullare, medullary, medullary cancer of thyroid gland, medullary thyroid, melanotic, meningeal, Merkel cell, metatypical cell, micropapillary, mucinous, cancer muciparum, cancer mucocellulare, mucoepidermoid, cancer mucosum, mucous, nasopharyngeal, neuroendocrine cancer of the skin, noninfiltrating, non-small cell, non-small cell lung cancer (NSCLC), oat cell, cancer ossificans, osteoid, Paget's, papillary, papillary cancer of thyroid gland, periampullary, preinvasive, prickle cell, primary intrasseous, renal cell, scar, schistosomal bladder, Schneiderian, scirrhous, sebaceous, signet-ring cell, cancer simplex, small cell, small cell lung cancer (SCLC), spindle cell, cancer spongiosum, squamous, squamous cell, terminal duct, anaplastic thyroid, follicular thyroid, medullary thyroid, papillary thyroid, trabecular cancer of the skin, transitional cell, tubular, undifferentiated cancer of thyroid gland, uterine corpus, verrucous, villous, cancer villosum, yolk sac, squamous cell particularly of the head and neck, esophageal squamous cell, and oral cancers and carcinomas.

Sarcomas that may be targeted include adipose, alveolar soft part, ameloblastic, avian, botryoid, sarcoma botryoides, chicken, chloromatous, chondroblastic, clear cell sarcoma of kidney, embryonal, endometrial stromal, epithelioid, Ewing's, fascial, fibroblastic, fowl, giant cell, granulocytic, hemangioendothelial, Hodgkin's, idiopathic multiple pigmented hemorrhagic, immunoblastic sarcoma of B cells, immunoblastic sarcoma of T cells, Jensen's, Kaposi's, kupffer cell, leukocytic, lymphatic, melanotic, mixed cell, multiple, lymphangio, idiopathic hemorrhagic, multipotential primary sarcoma of bone, osteoblastic, osteogenic, parosteal, polymorphous, pseudo-kaposi, reticulum cell, reticulum cell sarcoma of the brain, rhabdomyosarcoma, rous, soft tissue, spindle cell, synovial, telangiectatic, sarcoma (osteosarcoma)/malignant fibrous histiocytoma of bone, and soft tissue sarcomas.

Lymphomas that may be targeted include AIDS-related, non-Hodgkin's, Hodgkin's, T-cell, T-cell leukemia/lymphoma, African, B-cell, B-cell monocytoid, bovine malignant, Burkitt's, centrocytic, lymphoma cutis, diffuse, diffuse, large cell, diffuse, mixed small and large cell, diffuse, small cleaved cell, follicular, follicular center cell, follicular, mixed small cleaved and large cell, follicular, predominantly large cell, follicular, predominantly small cleaved cell, giant follicle, giant follicular, granulomatous, histiocytic, large cell, immunoblastic, large cleaved cell, large nocleaved cell, Lennert's, lymphoblastic, lymphocytic, intermediate; lymphocytic, intermediately differentiated, plasmacytoid; poorly differentiated lymphocytic, small lymphocytic, well differentiated lymphocytic, lymphoma of cattle; MALT, mantle cell, mantle zone, marginal zone, Mediterranean lymphoma mixed lymphocytic-histiocytic, nodular, plasmacytoid, pleomorphic, primary central nervous system, primary effusion, small b-cell, small cleaved cell, small concleaved cell, T-cell lymphomas; convoluted T-cell, cutaneous t-cell, small lymphocytic T-cell, undefined lymphoma, u-cell, undifferentiated, aids-related, central nervous system, cutaneous T-cell, effusion (body cavity based), thymic lymphoma, and cutaneous T cell lymphomas.

Leukemias and other blood cell malignancies that may be targeted include acute lymphoblastic, acute myeloid, acute lymphocytic, acute myelogenous leukemia, chronic myelogenous, hairy cell, erythroleukemia, lymphoblastic, myeloid, lymphocytic, myelogenous, leukemia, hairy cell, T-cell, monocytic, myeloblastic, granulocytic, gross, hand mirror-cell, basophilic, hemoblastic, histiocytic, leukopenic, lymphatic, Schilling's, stem cell, myelomonocytic, monocytic, prolymphocytic, promyelocytic, micromyeloblastic, megakaryoblastic, megakaryoctyic, rieder cell, bovine, aleukemic, mast cell, myelocytic, plamsa cell, subleukemic, multiple myeloma, nonlymphocytic, chronic myelogenous leukemia, chronic lymphocytic leukemia, polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, and myelodysplasia and chronic myelocytic leukemias.

Brain and central nervous system (CNS) cancers and tumors that may be targeted include astrocytomas (including cerebellar and cerebral), brain stem glioma, brain tumors, malignant gliomas, ependymoma, glioblastoma, medulloblastoma, supratentorial primitive neuroectodermal tumors, visual pathway and hypothalamic gliomas, primary central nervous system lymphoma, ependymoma, brain stem glioma, visual pathway and hypothalamic glioma, extracranial germ cell tumor, medulloblastoma, myelodysplastic syndromes, oligodendroglioma, myelodysplastic/myeloproliferative diseases, myelogenous leukemia, myeloid leukemia, multiple myeloma, myeloproliferative disorders, neuroblastoma, plasma cell neoplasm/multiple myeloma, central nervous system lymphoma, intrinsic brain tumors, astrocytic brain tumors, gliomas, and metastatic tumor cell invasion in the central nervous system.

Gastrointestinal cancers that may be targeted include extrahepatic bile duct cancer, colon cancer, colon and rectum cancer, colorectal cancer, gallbladder cancer, gastric (stomach) cancer, gastrointestinal carcinoid tumor, gastronintestinal carcinoid tumors, gastrointestinal stromal tumors, bladder cancers, islet cell carcinoma (endocrine pancreas), pancreatic cancer, islet cell pancreatic cancer, prostate cancer rectal cancer, salivary gland cancer, small intestine cancer, colon cancer, and polyps associated with colorectal neoplasia.

Lung and respiratory cancers that may be targeted include bronchial adenomas/carcinoids, esophagus cancer esophageal cancer, esophageal cancer, hypopharyngeal cancer, laryngeal cancer, hypopharyngeal cancer, lung carcinoid tumor, non-small cell lung cancer, small cell lung cancer, small cell carcinoma of the lungs, mesothelioma, nasal cavity and paranasal sinus cancer, nasopharyngeal cancer, nasopharyngeal cancer, oral cancer, oral cavity and lip cancer, oropharyngeal cancer; paranasal sinus and nasal cavity cancer, and pleuropulmonary blastoma.

Urinary tract and reproductive cancers that may be targeted include cervical cancer, endometrial cancer, ovarian epithelial cancer, extragonadal germ cell tumor, extracranial germ cell tumor, extragonadal germ cell tumor, ovarian germ cell tumor, gestational trophoblastic tumor, spleen, kidney cancer, ovarian cancer, ovarian epithelial cancer, ovarian germ cell tumor, ovarian low malignant potential tumor, penile cancer, renal cell cancer (including carcinomas), renal cell cancer, renal pelvis and ureter (transitional cell cancer), transitional cell cancer of the renal pelvis and ureter, gestational trophoblastic tumor, testicular cancer, ureter and renal pelvis, transitional cell cancer, urethral cancer, endometrial uterine cancer, uterine sarcoma, vaginal cancer, vulvar cancer, ovarian carcinoma, primary peritoneal epithelial neoplasms, cervical carcinoma, uterine cancer and solid tumors in the ovarian follicle), superficial bladder tumors, invasive transitional cell carcinoma of the bladder, and muscle-invasive bladder cancer.

Skin cancers and melanomas (as well as non-melanomas) that may be targeted include cutaneous t-cell lymphoma, intraocular melanoma, tumor progression of human skin keratinocytes, basal cell carcinoma, and squamous cell cancer. Liver cancers that may be targeted include extrahepatic bile duct cancer, and hepatocellular cancers. Eye cancers that may be targeted include intraocular melanoma, retinoblastoma, and intraocular melanoma Hormonal cancers that may be targeted include: parathyroid cancer, pineal and supratentorial primitive neuroectodermal tumors, pituitary tumor, thymoma and thymic carcinoma, thymoma, thymus cancer, thyroid cancer, cancer of the adrenal cortex, and ACTH-producing tumors.

Miscellaneous other cancers that may be targeted include advanced cancers, AIDS-related, anal cancer adrenal cortical, aplastic anemia, aniline, betel, buyo cheek, cerebriform, chimney-sweeps, clay pipe, colloid, contact, cystic, dendritic, cancer à deux, duct, dye workers, encephaloid, cancer en cuirasse, endometrial, endothelial, epithelial, glandular, cancer in situ, kang, kangri, latent, medullary, melanotic, mule-spinners', non-small cell lung, occult cancer, paraffin, pitch workers', scar, schistosomal bladder, scirrhous, lymph node, small cell lung, soft, soot, spindle cell, swamp, tar, and tubular cancers.

Miscellaneous other cancers that may be targeted also include carcinoid (gastrointestinal and bronchal) Castleman's disease chronic myeloproliferative disorders, clear cell sarcoma of tendon sheaths, Ewing's family of tumors, head and neck cancer, lip and oral cavity cancer, Waldenström's macroglobulinemia, metastatic squamous neck cancer with occult primary, multiple endocrine neoplasia syndrome, multiple myeloma/plasma cell neoplasm, Wilms' tumor, mycosis fungoides, pheochromocytoma, sezary syndrome, supratentorial primitive neuroectodermal tumors, unknown primary site, peritoneal effusion, malignant pleural effusion, trophoblastic neo-plasmas, and hemangiopericytoma.

The methods disclosed herein for singlet oxygen generation are useful in treating pathogenic infections, e.g., preventing, inhibiting and/or ameliorating a pathogenic infection or symptom of a pathogenic infection. In some cases, the methods and compounds disclosed herein are useful in treating a condition due to a pathogenic infection.

Contemplated diseases or disorders due to a pathogenic infection include gastroenteritis, encephalitis, respiratory tract infections (e.g., SARS, influenza), virus-induced cancers, rabies, hemorrhagic fevers (e.g., Crimean-Congo, Dengue), Rift valley fever, listeriosis, or toxoplasmosis. Also contemplated diseases or disorders due to a pathogenic infection include meningitis, myocarditis, hepatitis, bacterimia, and skin infections.

Contemplated pathogens include viral, bacterial, fungal, and parasitic pathogens. Contemplated pathogenic viruses include a calicivirus (e.g., norovirus, sapovirus), a picornavirus, a Togavirus, a Bunyavirus, a Rhabdovirus, a herpes virus, an adenovirus, an arterivirus, a coronavirus, a flavivirus, a paramyxovirus, a papillomavirus, a virus encoding for an ovarian tumor (OTU)-like protease, a baculovirus, or a nairovirus. Other contemplated pathogenic viruses include polyoma viruses and retroviruses.

Specific viruses contemplated include encephalomyocarditis virus (EMCV), Sindbis virus (SiNV), La Crosse virus (LaCV), Norwalk virus, Epstein-Barr (EBV), herpesvirus, Dengue virus, respiratory syncytial virus (RSV), papillomavirus, and influenza. Further specific viruses contemplated include cytomegalovirus, BK virus, hepatitis C virus, and HIV.

Contemplated bacteria include *Chlamydia, Escherichia, Salmonella, Yersinia, Burkholderia, Haemophilus, Listeria*, and *Mycobacterium*. Other bacteria contemplated include *Staphylococcus aureus*, or more specifically methicillin-resistant *Staph aureus* (MRSA).

Contemplated parasites or fungi include *Plasmodium falciparum, Toxoplasma gondii, Entamoeba histolytica, Giardia lamblia, Trypanosoma brucei, Trypanosoma cruzi, Cestoda, Clonorchis, Opisthorchis, Strongylocides, Candida, Aspergillus*, and *Cryptococcus*.

MNCs can be administered to the target area as a solution composition, as vapor composition under moderate temperature or embedded in a matrix, such as a polymer. Contemplated pharmaceutical compositions of MNCs include a pharmaceutically acceptable excipient. The term "pharmaceutically acceptable excipient" refers to an excipient for administration of a pharmaceutical agent, such as the MNCs described herein. The term refers to any pharmaceutical excipient that may be administered without undue toxicity. Excipients include carriers, solvents, stabilizers, adjuvants, diluents, etc.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

In some embodiments, the pharmaceutical composition is formulated to achieve a physiologically compatible pH, and may range from a pH of about 3 to a pH of about 11, about pH 3 to about pH 7, depending on the formulation and route of administration. In alternative embodiments, the pH is adjusted to a range from about pH 5.0 to about pH 8. More particularly, in various cases, the pharmaceutical compositions comprise a therapeutically or prophylactically effective amount of at least one MNC as described herein, together with one or more pharmaceutically acceptable excipients.

The composition comprising the MNC is administered by any route that permits treatment of the disease or condition.

One route of administration is oral administration. Additionally, the composition may be delivered to a patient using any standard route of administration, including parenterally, such as intravenously, intraperitoneally, intrapulmonary, subcutaneously or intramuscularly, intrathecally, topically, transdermally, rectally, orally, nasally or by inhalation. In some cases, the MNC as disclosed herein is embedded for in a polymer matrix of a biological degradable polymer, a water-soluble polymer or a mixture of both, and optionally suitable surfactants. Embedding can mean in this context the incorporation of the MNC in a matrix of polymers.

Additionally, in various embodiments, the pharmaceutical compositions are sterile injectable preparation, such as a sterile injectable aqueous emulsion or oleaginous suspension. This emulsion or suspension may be formulated by a person of ordinary skill in the art using those suitable excipients, such as dispersing or wetting agents and suspending agents, including those mentioned above. The sterile injectable preparation may also be a sterile injectable solution or suspension in a non-toxic parenterally acceptable diluent or solvent, such as a solution in 1,2-propane-diol.

In some cases, the sterile injectable preparation is prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

Material Coating Applications

The high absorption nature of MNCs disclosed herein allows for absorption of linear and non-linear excitation. MNCs are stable in solution and in air and can be used in the coating of materials that requires high absorption of photons, either solar or artificial.

One such application is the use of MNCs as coating that protects the underlying materials from photo damage, includes but not limited to a lens, a metal, a glass, or a detector. Concentration control of MNCs would also allow for variable protection of light, such as for use as a coating on windows or in a paint to, e.g., minimize fading. MNCs can also be coating to materials that require protection from high-intensity light, such as laser goggles.

The MNCs have non-linear properties such that the absorption of photons increase non-linearly with excitation, allowing for low absorption (high transparency) at lower intensity (such as sun light) and high absorption (low transparency) at high intensity (such as laser light). MNCs can be used in coatings for lens, and sensors which can easily be damage by high intensity light.

In various cases, the coating or film provides a first absorption ratio for a first wavelength range of 300 nm to 800 nm and a second absorption ratio for a second wavelength range of 800 nm to 2000 nm. For example, MNCs may be designed to provide two photon absorption (i.e., non-linear excitation) at wavelengths of 800 nm to 2000 nm, down converting the absorbed photons into photons emitted over the 400 nm to 1000 nm range. The thicknesses of MNC layers may be determined to achieve a desired absorption ratio of incident light. Applications of MNC layers include photolithography and microfabricaiton masks, optical power limiters, and optical imaging. For the optical imaging applications, and others, longer wavelength light is made incident on a MNC layer. These include ranges of light in the near infrared (e.g., 700 nm to 1400 nm), mid-infrared (e.g., 1400 nm to 8000 nm), and far-infrared (e.g., 8000 nm to 15000 nm). The MNC films may be formed by dispersing the functionalized MNCs in a solvent for forming the thin film. The film may then be formed by spin-coating or printing, after which standard lithography may be applied to pattern the film if desired, and the composite film is dried or cured. In other examples, the film may be formed by growth techniques. Yet other examples will become apparent to persons of ordinary skill in the art.

The small size and volume of MNCs allow for the coating to be made to be as thin as the cluster size, e.g., about 2 nm. Due to the high stability and high absorption nature of MNCs, this material can be mixed in with other materials that are not photo-stable to provide additional stability, such as photosensitive additives. Contemplated photosensitive additives include inorganic additives such as $C_{60}$ and metal nanoparticles; or organic chromophores such as porphyrins and chlorophylls. Specific examples of organic chromophores include photofrinI, photofrinII, methyl blue, new methyl blue, and rose Bengal.

Figure 9:
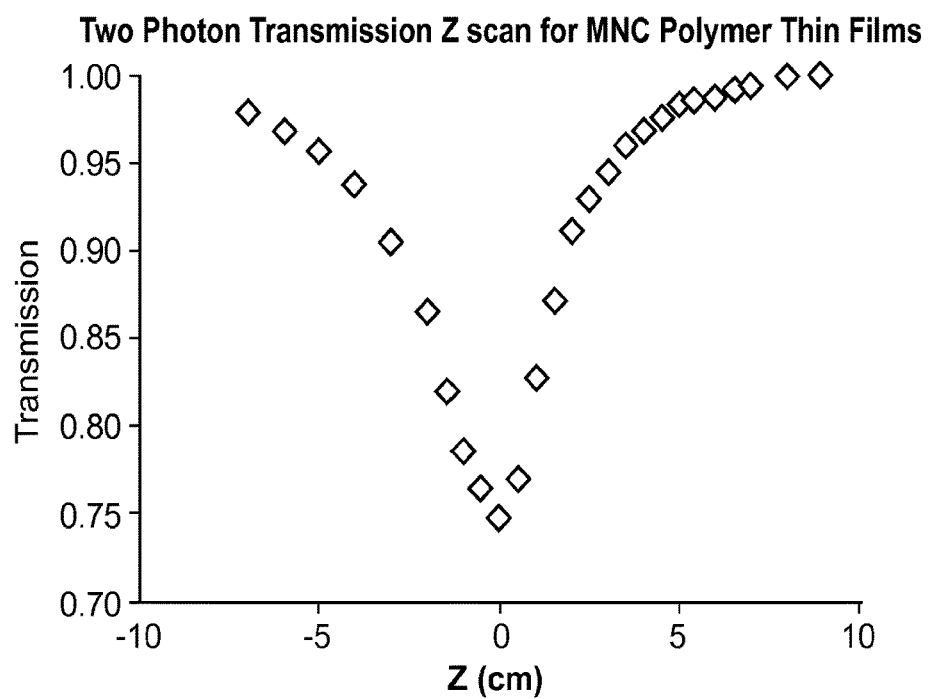
FIG. 9 shows a two-photon absorption Z scan for an MNC polymer thin film, under 800 nm excitation.

Au nanoclusters can be embedded in a polymer matrix and dried under controlled condition to produce free standing films. Two-photon excited absorption Z scan has been performed with the conjugate thin film shown in FIG. 9. The film has 100% transition under 800 nm excitation, and 75% transition under 800 nm two photon excitation, achieving optical transparence under low intensity and absorption under high intensity. The two-photon absorption cross-section was calculated to be $2.6 \times 10^6$ GM.

EXAMPLES

A solution containing metal ions, such as AuCl is cooled to a specific temperature (0° C. for Au) over 30 minute in an ice bath. The ligand in more than 1 equivalent mole of gold is added slowly to the solution. (The ligand equivalent will determine the cluster size synthesized). The solution is stirred for 30 minutes after which a strong reducing agent such as $NaBH_4$ in more than 1 equivalent per mole of gold is added. The reaction is stirred for 3 h. The ice bath was removed after the reaction and the solution was warmed to room temperature. The reaction was allowed to further proceed from 12-60 hours. The solution is washed with a polar methanol water mixture. Depending on the ligand polarity, the nanocluster can be collected either in the polar or non-polar solutions.

A solution of 1-pyrenecarboxylic acid (0.7 g, 2.8 mmol) in dichlormethane (30 ml) and oxalyl chloride (0.42 g, 3.4 mmol) is prepared and 0.15 ml of DMF is added, the reaction mixture was stirred for 2 hours at room temperature. After the reaction, the solvent was evaporated. The product was added to 20 ml of THF, which was added to a solution of cysteamine hydrochloride (0.29 g, 1.27 mmol) and sodium hydroxide (0.23 g, 5.7 mmol). The reaction mixture was stirred for 12 hours. The product is washed with water and THF, then filtered and added to a solution of sodium borohydride (0.96 g, 25.4 mmol), and stirred at 90 C for 2 hours. The final mixture is cooled to room temperature and pH adjusted to 2 with HCl. Solvent is removed, and the product is extracted with chloroform and dried. The final product is dissolved in hexane. $Au_{25}$ with 18 conjugates is synthesized starting with 0.5 g of $HAuCl_4$ dissolved in 10 mL solvent of $H_2O$, 0.9 g of TOABr in 40 mL toluene is added to the reaction. The solution was placed in an ice bath. The conjugated (N-(2-mercaptoethyl)pyrene-1-carboxamide) was added to the solution in excess and stirred. A freshly prepared $NaBH_4$ solution (0.485 g, 10 mL $H_2O$) was quickly added. The solution turned black and the reaction was allowed to stir for 30 min. The aqueous phase was removed and the toluene solution was washed with copious amount of water. The metal nanocluster conjugates were extracted with acetone. The acetone was evaporated and the metal nanocluster conjugates were washed with ethanol and acetonitrile. After the synthesis of the metal nanocluster conjugate, the ligand on the conjugate can be made with a terminal group that allows for further modification. For example a carboxylic acid ligand group can be substituted to an amide group via a amide-forming coupling reaction. The metal nanocluster conjugate is dissolved in THF and treated with 20 equivalent of BOP HOBt NMM and DMAP for the carbon activation. After the activation, a 10 equivalents of amine is added and stirred for 15 hours. The resulted solution is dried to remove the solvent and additional solvent washes were used to achieve high purity. Complete conjugate on a Metal nanocluster conjugate can be exchanged. The metal nanocluster conjugate and the new conjugate is solvated in the same solvent. The exchange can occur through thermos dynamic means in room temperature. For example $Au_{25}$ with a simple conjugate compost of a thiol, a 4 carbon chain and a benzene can be changed to a cognate of N-(2-mercaptoethyl)pyrene-1-carbozamide. The $Au_{25}$ conjugate and the new conjugate is mixed in a 1:5 molar ration in toluene. The reaction mixture is stirred for 2 hours. The resultant solution was then ultra-centrifuged and washed with toluene repeatedly to free from the excess ligand.

REFERENCES (1) Yau, et al. An Ultrafast Look at Au Nanoclusters. Accounts of chemical research 2013.
(2) Yau, et al. The Journal of Physical Chemistry C 2010, 114, 15979-15985.
(3) Yau, et al. Nanoscale 2012, 4, 4247-54.
(4) Ramakrishna, et al. Journal of the American Chemical Society 2008, 130, 5032-3.
(5) Varnayski, et al. ACS nano 2010, 4, 3406-12.
(6) Varnayski, et al. Journal of the American Chemical Society 2010, 132, 16-7.
(7) Devadas, et al. The Journal of Physical Chemistry C 2010, 114, 22417-22423.
(8) Varnayski, et al. The Journal of Chemical Physics 2001, 114, 1962.
(9) Goodson, et al. International Reviews in Physical Chemistry 2004, 23, 109-150.
(10) Mroz, et al. Cancers 2011, 3, 2516-39.

What is claimed:

1. A conjugate comprising a metal nanocluster having at least a portion of the surface of the metal nanocluster modified with a moiety having a structure -X-Lk-Lg;
   wherein
   the metal nanocluster comprises $Au_{144}$, $Ag_{32}$, or a combination thereof;
   Lk is $C_{1-50}$alkylene, wherein the carbon backbone optionally has one or more heteroatoms selected from O, NH, and S;
   X is a functional group capable of attaching to the metal nanocluster surface; and
   Lg is a ligand selected from the group consisting of a peptide, a protein, an oligonucleotide, a fluorophore, and a chromophore.

2. The conjugate of claim 1, wherein X comprises an alcohol, an ether, a thiol, a phosphate, a phosphonate, phosphinate, or a carboxylate.

3. The conjugate of claim 1, wherein the metal nanocluster is $Au_{144}$.

4. The conjugate of claim 1, wherein Lg is a two-photon chromophore.

5. The conjugate of claim 1, wherein Lg is a fluorophore.

6. A composition comprising the conjugate of claim 1 in a liquid.

7. A composition comprising the conjugate of claim 1 in the form of a coating or a film.

8. The composition of claim 7, wherein the film comprises a polymer selected from the group consisting of polyvinylpyrrolidone, polyvinyl alcohol, poly-methyl methacrylate, polystyrene, polyethylene oxide, polyethylene glycol, and a mixture thereof.

9. The composition of claim 7, further comprising a photosensitive additive.

10. The conjugate of claim 1, wherein the metal nanocluster exhibits an absorption to volume ratio of at least $10^7$ $m^{-1}$ under linear or non-linear excitation, has an excited state longer than 10 psec, and exhibits no plasmon resonance.

* * * * *